United States Patent
Herradon Garcia et al.

(10) Patent No.: US 7,476,754 B2
(45) Date of Patent: Jan. 13, 2009

(54) BIPHENYL DERIVED THIAMIDES AS CALPAIN INHIBITORS

(75) Inventors: Bernardo Herradon Garcia, Madrid (ES); Mercedes Alonso Giner, Madrid (ES); Esperanza Benito Cano, Madrid (ES); Antonio Chana Lopez, Madrid (ES); Ana Montero Aguado, Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 11/579,737

(22) PCT Filed: May 6, 2005

(86) PCT No.: PCT/ES2005/070058

§ 371 (c)(1),
(2), (4) Date: Feb. 20, 2007

(87) PCT Pub. No.: WO2005/108354

PCT Pub. Date: Nov. 17, 2005

(65) Prior Publication Data
US 2007/0270480 A1    Nov. 22, 2007

(30) Foreign Application Priority Data
May 7, 2004    (ES) ............................... 200401104

(51) Int. Cl.
| C07C 205/00 | (2006.01) |
| C07C 69/76  | (2006.01) |
| C07C 327/00 | (2006.01) |
| C07C 321/00 | (2006.01) |
| C07C 235/00 | (2006.01) |
| C07C 315/00 | (2006.01) |
| C07C 63/33  | (2006.01) |

(52) U.S. Cl. .................. 560/102; 560/21; 560/16; 562/426; 562/427; 562/492; 564/162; 564/163; 564/74

(58) Field of Classification Search .................. None
See application file for complete search history.

(56) References Cited

U.S. PATENT DOCUMENTS

| 5,541,290 A | 7/1996 | Harbeson et al. |
| 5,554,767 A | 9/1996 | Wang et al. |

FOREIGN PATENT DOCUMENTS

| EP | 0 743 293 | 11/1996 |
| ES | 2 219 187 | 11/2004 |
| WO | 03/014088 | 2/2003 |
| WO | 2004/101494 | 11/2004 |
| WO | 2004101494 | * 11/2004 |

OTHER PUBLICATIONS

Montero et al., Bioorganic & Medicinal Chemistry Letters, 2004, 14, 11, pp. 2753-2757.*
Montero et al., and Chemistry and Biodiversity, 2004, 1, 3, pp. 442-457.*
Mann et al., Helv. Chim. Acta., 2002, 85, 11, pp. 3624-3638.*
Enrique Mann et al., "Synthesis and Crystal Structure of Peptide-2,2'-Biphenyl Hybrids", Helvetica Chimica Acta, vol. 85 (2002), pp. 3624-3638.
Ana Montero et al., "Peptide-Biphenyl Hybrids as Calpain Inhibitors", Chemistry & Biodiversity, vol. 1 (2004), pp. 442-457.
Ana Montero et al., "Student on Aromatic Compounds: Inhibition of Calpain I by Biphenyl Derivatives and Peptide-Biphenyl Hybrids", Bioorganic & Medical Chemistry Letters 14 (2004) pp. 2753-2757.
S. Scheibye et al., "Studies on Organophosphorus Compounds XXI. The Dimer of p-Methoxyphenylthionophosphine Sulfide as Thiation Reagent. A New Route to Thiocarboxamides", Bull. Soc. Chim. Belg., vol. 87 (3), pp. 229 to 238 (1978).
Ernest Schaumann, "Synthesis of Thioamides and Thiolactams", Comprehensive Organic Synthesis, vol. 6, pp. 419-434 (1991).
Kevin K.W. Wang et al., "Development and Therapeutic Potential of Calpain Inhibitors", Adv. Pharmacol., vol. 37, pp. 117-152 (1996).
Enrique Mann et al., "Novel Peptide-Heterocycle Hybrids: Synthesis and Preliminary Studies on Calpain Inhibition", Adv. Synth. Catal., vol. 344, No. 8, pp. 855-867 (2002).

Geraldine C.B. Harriman et al., "Cell Adhesion Antagonists: Synthesis and Evaluation of a Novel Series of Phenylalanine Based Inhibitors", Bioorganic & Medicinal Chemistry Letters, vol. 10, pp. 1497-1499 (2000).
Shoji Hata et al., "Domain II of m-calpain is a $Ca^{2+}$ -dependent cysteine protease", FEBS Letters, vol. 501, pp. 111-114 (2001).
Arnaud LeTiran et al., "Design and Evaluation of Affinity Labels of Functionalized Amino Acid Anticonvulsants", J. Med. Chem., vol. 45, pp. 4762-4773 (2002).
Paul Lloyd-Williams et al., "Chemical Approaches to the Synthesis of Peptides and Proteins", (CRC Press, Boca Raton 1997).
Philip J. Hajduk et al., Privileged Molecules for Protein Binding Identified from NMR-Based Screening, J. Med. Chem. vol. 43, pp. 3443-3447 (2000).
B.M. Trost et al., "Comprehensive Organic Synthesis", Pergamon Press (1991) and http://www.elsevier.com/wps/find/bookdescription.cws_home/26507/...
Frank J.E. Vajda, "Neuroprotection and neurodegenerative disease", Journal of Clinical Neuroscience 9(1), pp. 4-8.[2002].
Tatiana G. Sazontova et al., "Calpains: physiological and pathophysiological significance", Pathophysiology 6, pp. 91-102 (1999).
Adam Doble, "The Role of Excitotoxicity in Neurodegenerative Disease: Implications for Therapy", Pharmacol. Ther., vol. 81, No. 3, pp. 163-221 (1999).
Patrick Metzner, "Thiocarbonyl Compounds as Specific Tools for Organic Synthesis", Topics in Current Chemistry, vol. 204, pp. 128-181 (1999).
Yuanhui Huang et al., "The calpain family and human trends", Trends in Molecular Medicine, vol. 7, No. 8, pp. 355-362 (Aug. 2001).
Paolo Calabresi et al., "Ionotropic glutamate receptors: still a target for neuroprotection in brain ischemia? Insights from in vitro studies", Neurobiology of Disease, vol. 12(1), pp. 82-88 (2003) (Abstract).
Swapan K. Ray et al., "Calpain in the pathophysiology of spinal cord injury: neuroprotection with calpain inhibitors", Brain Research Reviews, vol. 42, pp. 169-185 (2003).

\* cited by examiner

*Primary Examiner*—Karl J Puttlitz
(74) *Attorney, Agent, or Firm*—Wenderoth, Lind and Ponack, L.L.P.

(57) ABSTRACT

The present invention relates to compounds derived from biphenyl with activity as calpain inhibitors. One compound of the present invention is a 2,2'-disubstituted biphenyl, where the substituents in the 2 and 2' positions of the biphenyl skeleton are chains containing structures related to amino acids, including fragments of aminocarbonylic compounds where at least one of the substituents in said 2- or 2'-positions is bonded to the biphenyl skeleton via a thiocarbonyl group, forming compounds with thioamide functionality. The present invention also encompasses any of the conformational isomers (atropisomers) of said compound of formula I. The compounds of formula I have application in the preventive or therapeutic treatment of a degenerative disease.

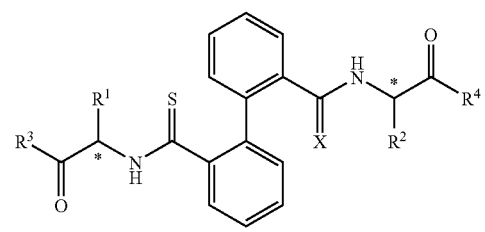

4 Claims, 1 Drawing Sheet

BIPHENYL DERIVED THIAMIDES AS CALPAIN INHIBITORS

FIELD OF THE ART

The present invention comes with the field of enzyme inhibitors with therapeutic activity, more specifically calpain inhibitors.

STATE OF THE ART

Calpains, or calcium activated neutral proteases (II) (CANP, E.C. 3.4.22.17), are a family of proteases with cysteine ("cysteine proteases") with a very active metabolic role. Although their natural substrate has not been clearly determined, these enzymes catalyse the hydrolysis of a variety of proteins involved in the transduction of signals, in the reconstruction of the cytoskeleton, in the regulation of the cell cycle and in apoptosis (Adv. Pharmacol. 1996, 37, 117). In mammals, the calpains family includes various tissue-specific isofoms and two ubiquitous isoenzymes: µ-calpain (or calpain I) and m-calpain (or calpain II), which require micromolar and millimolar quantities respectively of calcium (II) for their activation. Structural studies using X-ray diffraction have shown that each isoform consists of a large subunit (~80 kDa), which presents a cysteine protease domain of the papain type, and a small subunit (~30 kDa), which is common to each isoenzyme. The C-terminal ends of each subunit have domains capable of bonding to Ca (II) (calmoduline type domain) (FEBS Lett. 2001, 501, 111).

The overactivation of calpains, which can occur when the intracellular concentration of calcium (II) increases, is involved in numerous diseases, such as cerebral and cardiac ischaemias, Alzheimer, Parkinson, muscular distrophy, cataracts, demyelinating diseases (such as multiple sclerosis) and other degenerative diseases (Pathophysiology 1999, 6, 91; Brain Res. Rev. 2003, 42, 169).

The main application of selective inhibitors of calpain is as neuroprotector agents. In the therapeutic area related to neuroprotection, a range of strategies has been used so far. Agents have been used which act on the membrane depolarisation and the entry of calcium into cells, or which prevent the production of free radicals (antioxidants), or which are antagonists of the action of neurotransmitters (J. Clinical Neurosci. 2002, 9, 4). A great deal of attention has recently been paid to drugs capable of blocking the NMDA receptors for glutamate; nevertheless, the blocking of ionotropic receptors of excitatory amino acids cannot be an ideal method for preventing excitotoxic action since these drugs have psychotomimetic side effects (Pharmacol. Ther. 1999, 81, 163; Neurobiol. Disease 2003, 12, 82). An interesting alternative for achieving neuroprotection is the blocking of "post-receptor" cell phenomena which are physiologically silenced, in other words, the search for selective blockers of catabolic cascades induced by excitotoxic agents. These potential drugs with intracellular action could, when acting on metabolic routes which are activated during neurodegeneration, foreseeably permit a more efficient and selective neuroprotector action.

The overactivation of calpain requires a continual increase in the intracellular concentrations of Ca (II), and this enzyme is latent in cells at rest [in other words, with "normal" Ca (II) levels]. Therefore, the inhibition of calpain is presented as a suitable treatment in neurodegenerative diseases. On the basis of its characteristics, the inhibition of calpain would foreseeably have fewer side effects in human therapeutics than the blocking of metabolic processes prior to their activation in pathological processes, as is the case with antagonism of the NMDA receptor of glutamate and aspartate, due to the fact that calpain is not activated under "normal" physiological conditions and that the action of excitatory amino acids is essential for the normal functioning of the nervous system.

Moreover, powerful and selective inhibitors of calpain are very useful as work tools for studying the action mechanism of this protease, along with its role in certain physiological processes.

Moreover, biphenyls substituted in different ways have been used as pharmacophores with a range of different biological activities (J. Med. Chem. 2000, 43, 3443). In addition, biphenyl derivatives have been used as mesogenic fragments for the preparation of liquid crystals (EP-743293). On the other hand, amino acids and related compounds, such as aminocarbonylic compounds, possess a range of different biological properties (J. Med. Chem. 2002, 45, 4762; Bioorg. Med. Chem. Lett. 2000, 10, 1497).

Reversible and irreversible inhibitors of calpain have been described (Trends Mol. Medicine 2001, 7, 355; U.S. Pat. No. 5,541,290). The most frequent structural features of these inhibitors is that they are peptides or peptidomimetics with few amino acids (between 2 and 6), hydrophobic and with some electrophile functionality, among which can be mentioned α-ketophophonates, α-ketophophinates, oxides of α-ketophophines, α-ketoesters, α-ketoacids, α-ketoamides, trifluoromethylketones, aldehydes, methylsulphonium salts, epoxides, etc. These compounds apparently act on the papain type domain of the calpain, which leads to a relatively low selectivity, due to which they are frequently also inhibitors of other cysteine proteases (for example, papain) and even serine proteases. Due in part to these drawbacks, a calpain inhibitor having therapeutic utility has not yet been found.

There exists a need to find calpain inhibitors having therapeutic utility. One type of calpain inhibitor that has not yet been described and which has not been investigated previously consists of derivatives of 2,2'-disubstituted biphenyl, where the substituents in the 2- and 2'-positions are fragments derived from amino acids and related compounds, such as aminocarbonylic compounds where at least one of the substituents in the 2- and 2'-positions is bonded via a thiocarbonyl group, forming the thioamide functionality, are which are the object of this invention.

Recently, Spanish application (P-200301125) described the synthesis and biological evaluation of calpain inhibitors which are structurally derived from biphenyl with aminocarbonyl (carbamoyl) or carbonylamine substituents, indifferently, in the 2- and 2'-positions of the biphenyl system (Bioorg. Med. Chem. Lett. 2004, 14, 2753; Chemistry & Biodiversity 2004, 1, 442).

BRIEF DESCRIPTION OF THE INVENTION

The present invention relates to compounds derived from biphenyl with activity as calpain inhibitors. One compound of the present invention is a 2,2'-disubstituted biphenyl, where the substituents in the 2 and 2' positions of the biphenyl skeleton are chains containing structures related to amino acids, including fragments of aminocarbonylic compounds where at least one of the substituents in said 2- or 2'-positions is bonded to the biphenyl skeleton via a thiocarbonyl group, forming compounds with thioamide functionality.

DESCRIPTION

The present invention relates to a compound of formula I, which has a 2,2'-disubstituted biphenyl structure,

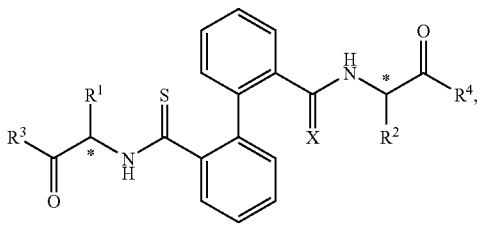

I wherein:
- the group X is oxygen (O) or sulphur (S), indifferently,
- the groups $R^1$ and $R^2$ are the same or different and are independent selected from among the groups H, alkyl of between 1 and 10 carbon atoms, aryl, or arylalkyl, when applicable (that is, when $R^1$ or $R^2 \neq H$), the asterisk (*) represents a stereogenic center, of configuration (R) or (S), indifferently,
- the groups $R^3$ and $R^4$ are the same or different and are independent selected from among the groups
  H,
  alkyl of between 1 and 6 carbon atoms,
  aryl,
  arylalkyl,
  $NH_2$,
  $NHR^5$ in which $R^5$ represents an alkyl or aryl group,
  $NR^6R^7$ in which $R^6$ and $R^7$ represent two alkyl or aryl groups, identical or different, or forming a cyclic system,
  OH,
  $OR^8$ in which $R^8$ represents an alkyl or aryl group; and
  any of the conformational isomers (atropisomers) of said compound of formula I.

The following are preferred compounds:
Methyl (S,S)-3-phenyl-2-{[2'-(2-phenyl-1-methoxycarbonyl-ethylthio-carbamoyl)-biphenyl-2-carbothiol]-amino}-propionate (1).
Methyl (S,S)-3-phenyl-2-{[2'-(2-phenyl-1-methoxycarbonyl-ethylthio-carbamoyl)-biphenyl-2-carbonyl]-amino}-propionate (2).
Methyl (S,S)-3-(1H-Indol-3-yl)-2-{[2'-(2-(1H-Indol-3-yl)-1-methoxycarbonyl-ethylcarbamoyl)-biphenyl-2-carbothiol]-amino}-propionate (3).
Methyl (S,S)-3-(1H-Indol-3-yl)-2-{[2'-(2-(1H-Indol-3-yl)-1-methoxycarbonyl-ethylcarbamoyl)-biphenyl-2-carbonyl]-amino}-propionate (4).
Methyl (S,S)-2-{[2'-(1-methoxycarbonyl-2-methyl-propylthiocarbamoyl)-biphenyl-2-carbothiol]-amino}-3-methyl-butyrate (5).
Methyl (S,S)-2-{[2'-(1-methoxycarbonyl-2-methyl-propylthiocarbamoyl)-biphenyl-2-carbonyl]-amino}-3-methyl-butyrate (6).
Methyl (S,S)-3-(4-hydroxy-phenyl)-2-{2'-[2-(4-hydroxy-phenyl)-1-methoxycarbonyl-ethylthiocarbamoyl]-biphenyl-2-carbothiol]-amino}-propionate (7).
Methyl (S,S)-3-(4-hydroxy-phenyl)-2-{2'-[2-(4-hydroxy-phenyl)-1-methoxycarbonyl-ethylthiocarbamoyl]-biphenyl-2-carbonyl]-amino}-propionate (8).

The synthesis of compounds of general formula I of the present invention has been carried out using the methods habitual in organic synthesis, which are known to experts in the art, and which involve the thionation reaction of the corresponding amides using any of the methods described in the bibliography for the synthesis of thioamide (*Topics Current Chemistry* 1999, 2047, 127; *Comprehensive Organic Synthesis*. vol 6 p. 419, Pergamon Press, 1991), among which can be mentioned the use of Laweson's reagent ([2,4-bis(4-methoxyphenyl)-1,3-dithia-2,4-diphosphethane-2,4-disuphide] (*Bull. Soc. Chim. Belg.* 1978, 87, 229). As substrates for the thionation reaction the corresponding amides II are used,

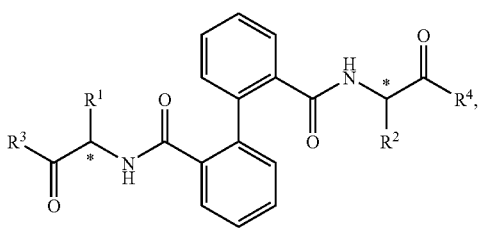

II which are prepared by acylation reaction between an acid or acid derivative, as electrophile, and an amine, as nucelophile, using methodologies habitual in organic synthesis, and which are known to experts in the art, (*Chemical Approaches to the Synthesis of Peptides and Proteins*. CRC Press, Boca Ratón, 1997; *Comprehensive Organic Synthesis*. vol 6, Pergamon Press, 1991).

An essential characteristic of the compounds of the present invention is that they are calpain inhibitors. There exist various isoforms of calpain, which are structurally very similar to each other and, as far as is known, share the same action mechanism. The two most abundant are micro-calpain (or calpain I) and milli-calpain (or calpain II), which are differentiated in in vitro tests in the concentration of calcium necessary for their activation. As the two isoforms of the enzyme are very similar to each other, it has been found in many examples of the bibliography that the calpain inhibitors consist of both enzymes (*Adv. Synth. Catal.* 2002, 344, 855). So, in the present invention, when we mention calpain, we are referring to the two isoforms (or isoenzymes) which are included in the definition of calpain. Therefore, another object of the present invention is the use of a compound of formula I as calpain inhibitor.

The calpain inhibition capacity has been quantified in terms of the value of $IC_{50}$, which is defined as the concentration of inhibitor that reduces the catalytic activity of an enzyme by half. The lower the value of $IC_{50}$, the more powerful the inhibitor. Inhibition results on calpain I (the most relevant from a physiological point of view) of some compounds of the present invention are shown in table 1 and in FIG. 1. Given that calpain II, also known as milli-calpain, needs a greater amount of calcium for activation, it might not possibly have such a relevant physiological role since such a concentration of calcium would cause cell death before the milli-calpain could become activated. For this reason, the inhibition tests have been performed for calpain I, though they can be extrapolated for calpain II.

TABLE 1

Inhibition results on calpain of compounds forming the object of this invention

| Compounds | $IC_{50}$ |
|---|---|
| 1 | 94 µM |
| 2 | 63 µM |
| 3 | 38 pM (=0.038 nM) |
| 4 | 69 nM |

TABLE 1-continued

Inhibition results on calpain of compounds forming the object of this invention

| Compounds | IC$_{50}$ |
|---|---|
| 5 | 71 nM |
| 6 | 52 pM (=0.052 nM) |
| 7 | 796 nM |
| 8 | 12 μM |

Some of the thioamides represented in FIG. 1 are the most potent calpain inhibitors described, and they mark a path for the design of therapeutically useful compounds. Owing to the fact that it has been found that overactivation of calpain is involved in numerous degenerative diseases, an additional object of the present invention is the use of a compound of formula I for the treatment or prevention of degenerative diseases and for preparing a drug for the preventive or therapeutic treatment of a degenerative disease, and especially when the degenerative disease is selected from among cerebral ischaemia, cardiac ischaemia, Alzheimer, Parkinson, muscular distrophy, cataracts and demyelinating diseases, and especially if the demyelinating disease is multiple sclerosis.

EXAMPLES

Figure 1:
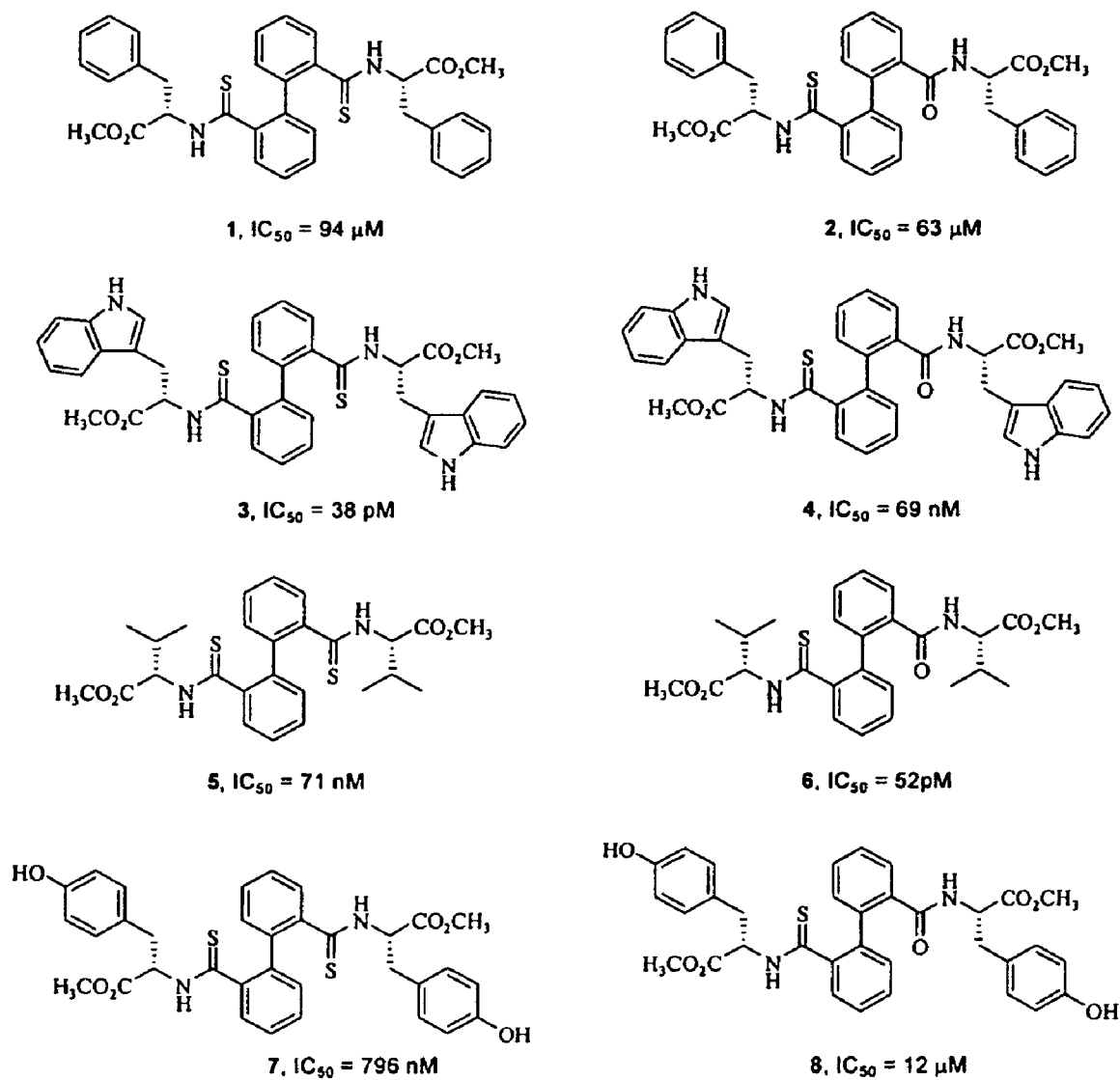
FIG. 1 shows results of the study on biphenyl derived thioamides forming the object of the present invention, and their biological activity as inhibitors of calpain I.

As illustrative examples, though without being limiting, the experimental procedures and spectroscopic and analytical data of some thioamides of formula I are given, along with tests on their biological activity.

Example 1

General Procedure for the Synthesis of Thioamides

On a solution of the corresponding bisamide derived from biphenyl (compounds of type A, 0.35 mmol, 1 equiv.) in toluene (10 ml), small portions of Lawesson's reagent were added (0.78 mml, 1.1 equiv.). The reaction mixture was stirred at reflux for 2 hours. The evaporation of the solvent gave rise to a residue which was purified by means of column chromatography in order to give the corresponding dithioamides (compounds of type B), together with monothioamides (compounds of type C), which were purified. by means of column chromatography as indicated in each case.

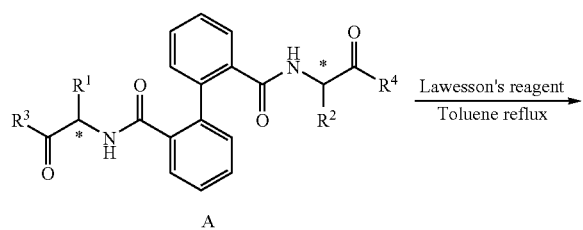

A

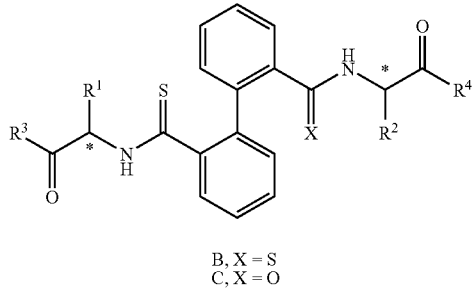

B, X = S
C, X = O

Example 2

Methyl (S,S)-3-phenyl-2-{[2'-(2-phenyl-1-methoxy-carbonyl-ethylthio-carbamoyl)-biphenyl-2-car-bothiol]-amino}—propionate (1)

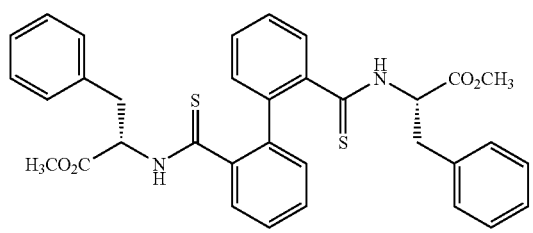

1

Following the general procedure, it was synthesised together with compound 2, with a yield of 54% after column chromatography (hexane/AcOEt gradient: 9/1 up to hexane/AcOEt gradient: 1/1). Pale yellow solid.

$[\alpha]^{25}_D$=−3 (c=0.33, MeOH).

$^1$H-NMR (300 MHz, CDCl$_3$, 30° C. mixture of conformers A+a, 1.2:1) δ: 9.00 (d, 1.1H, J$_{NH,CH\alpha}$=7.0, NH, a), 9.89 (d, 1.1H, J$_{NH,CH\alpha}$=7.0, NH, A), 7.47-7.23 (m, 12H, H$_{arom}$, A+a), 7.35-7.05 (m, 6H, H$_{arom}$, A+a), 5.40 (m, 0.9H, CH$_\alpha$-Phe, a), 5.24 (m, 1.1H, CH$_\alpha$-Phe, A), 3.67 (s, 3.2H, CO$_2$CH$_3$, A), 3.58 (s, 2.8H, CO$_2$CH$_3$, a), 3.25 (A of ABX, 0.9H, J$_{H\alpha,H\beta}$=13.9, J$_{H\alpha,CH\alpha}$=8.1, C(H$_\alpha$H$_\beta$)-Phe, a), 3.14 (B of ABX, 0.9H, J$_{H\beta,H\alpha}$=13.9, J$_{H\beta,CH\alpha}$=5.2, C(H$_\alpha$H$_\beta$)-Phe, a), 2.95 (A of ABX, 1.1H, J$_{H\alpha,H\beta}$=13.9, J$_{H\alpha,CH\alpha}$=8.1, C(H$_\alpha$H$_\beta$)-Phe, A), 2.81 (B of ABX, 1.1H, J$_{H\beta,H\alpha}$=5.2, J$_{H\alpha,CH\alpha}$=8.1, C(H$_\alpha$H$_\beta$)-Phe, A), ppm $^{13}$C-NMR (75 MHz, CDCl$_3$, 30° C. mixture of conformers A+a) δ: 200.2 (s, CS, a), 200.0 (s, CS, A), 170.8 (s, CO, A), 170.7 (s, CO, a), 141.7 (s, C$_{arom}$, a), 141.6 (s, C$_{arom}$, A), 137.2 (s, C$_{arom}$, A), 137.0 (s, C$_{arom}$, a), 135.6 (s, 2C, C$_{arom}$, A+a), 130.1 (d, C$_{arom}$), 129,7 (d, C$_{arom}$), 129.2 (d, C$_{arom}$), 129.1 (d, C$_{arom}$), 129.0 (d, C$_{arom}$), 128.6 (d, C$_{arom}$), 127.9 (d, C$_{arom}$), 127.7 (d, C$_{arom}$), 127.5 (d, C$_{arom}$), 127.4 (d, C$_{arom}$), 127.2 (d, C$_{arom}$), 59.2 (d, CH$_\alpha$-Phe, A), 59.0 (d, CH$_\alpha$-Phe, a), 52.5 (c, CO$_2$CH$_3$, a), 52.3 (c, CO$_2$CH$_3$, A), 36.8 (t, CH$_2$-Phe, a), 36.4 (t, CH$_2$-Phe, A), ppm IR v 3436, 3025, 2951, 1743, 1631, 1530, 1496, 1434, 1374, 1215, 956, 749 700 cm$^{-1}$.

ME (ES$^+$), m/e=597 ([MH]$^+$, 100%).

EA calculated for $C_{34}H_{32}N_2O_4S_2$: C, 68.43; H, 5.40; N, 4.69; S, 10.75. Found: C, 68.25; H, 5.19; N, 4.61; S, 10.51.

Example 3

Methyl (S,S)-3-phenyl-2-{[2'-(2-phenyl-1-methoxy-carbonyl-ethylthio-carbamoyl)-biphenyl-2-carbonyl]-amino}-propionate (2)

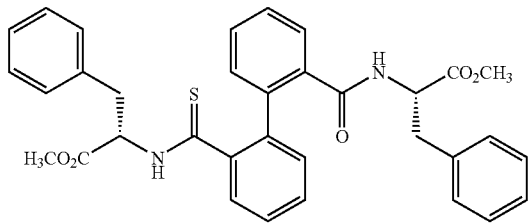

It was synthesised together with compound 2, following the general procedure indicated in example 1. A yield of 45% after purification in column (hexane/AcOEt gradient: 9/1 up to hexane/AcOEt gradient: 1/1). Pale yellow solid.

$[\alpha]_D = -10$ (c=0.11, MeOH).

$^1$H-NMR (400 MHz, CDCl$_3$, 30° C. mixture of conformers A+a, 4:3) δ: 10.02 (d, 0.57H, $J_{NH,CH\alpha}$=7.5, NH-Phe$_2$, A), 9.89 (d, 0.43H, $J_{NH,CH\alpha}$=7.5, NH-Phe$_2$, a), 7.61 (dd, 0.57H, $J_{ortho}$=7.7, $J_{meta}$=1.5, H$_{arom}$, A), 7.49 (dd, 0.43H, $J_{ortho}$=7.7, $J_{meta}$=1.5, H$_{arom}$, a), 7.44-7.15 (m, 15H, H$_{arom}$, A+a), 7.11 (dd, 0.57H, $J_{ortho}$=8.1, $J_{meta}$=1.5, H$_{arom}$, A), 7.07 (dd, 0.43H, $J_{ortho}$=7.8, $J_{meta}$=1.8, H$_{arom}$, a), 7.05 (dd, 0.43H, $J_{ortho}$=7.8, $J_{meta}$=1.9, H$_{arom}$, a), 6.96 (dd, 0.57H, $J_{ortho}$=8.1, $J_{meta}$=1.4, H$_{arom}$, A), 6.93 (d, 0.43H, $J_{NH,CH\alpha}$=7.4, NH-Phe$_1$, a), 6.93 (d, 0.57H, $J_{NH,CH\alpha}$=7.4, NH-Phe$_1$, A), 5.24 (X of ABX, 0.57H, CH$_\alpha$-Phe$_1$, A), 5.12 (X of ABX, 0.43H, CH$_\alpha$-Phe$_2$, a), 4.84 (X' of A'B'X', 1H, CH$_\alpha$-Phe$_1$, A+a), 3.71 (s, 1.71H, CO$_2$CH$_3$-Phe$_2$, A), 3.66 (s, 1.29H, CO$_2$CH$_3$-Phe$_2$, a), 3.52 (s, 1.71H, CO$_2$CH$_3$-Phe$_1$, A), 3.40 (s, 1.29H, CO$_2$CH$_3$-Phe$_1$, a), 3.23 (A' of A'B'X', 0.57H, $J_{H,H}$=13.9, C(H$_\alpha$H$_\beta$)-Phe$_1$, A), 3.04 (m, 0.57H, C(H$_\alpha$H$_\beta$)-Phe$_1$, A; 0.86H, CH$_2$-Phe$_1$, a; 0.86H, CH$_2$-Phe$_2$, a); 2.43 (A of ABX, 0.57H, $J_{H\alpha,H\beta}$=13.7, $J_{H\alpha,CH\alpha}$=7.8, C(H$_\alpha$H$_\beta$)-Phe$_2$, A); 2.31 (B of ABX, 0.57H, $J_{H\beta,H\alpha}$=13.7, $J_{H\beta,CH\alpha}$=5.2, C(H$_\alpha$H$_\beta$)-Phe$_2$, A), ppm.

$^{13}$C-NMR (75 MHz, CDCl$_3$, 30° C. mixture of conformers A+a, 4:3) δ: 200.4 (s, CS, a), 199.8 (s, CS, A), 171.9 (s, CO, a), 171.6 (s, CO, A), 170.7 (s, CO, A), 170.5 (s, CO, a), 169.7 (s, CO, a), 169.6 (s, CO, A), 142.3 (s, C$_{arom}$, a), 142.2 (s, C$_{arom}$, A), 139.7 (s, C$_{arom}$, a), 139.2 (s, C$_{arom}$, a), 136.2 (s, C$_{arom}$, a), 136.1 (s, C$_{arom}$, A), 136.0 (s, 2C, C$_{arom}$, A), 135.7 (s, 2C, C$_{arom}$, a), 134.9 (s, C$_{arom}$, a), 134.5 (s, C$_{arom}$, A), 130.4 (d, C$_{arom}$), 130.34 (d, C$_{arom}$), 130.0 (d, C$_{arom}$), 129.9 (d, C$_{arom}$), 129.4 (d, C$_{arom}$), 129.3 (d, C$_{arom}$), 129.22 (d, C$_{arom}$), 129.1 (d, C$_{arom}$), 128.9 (d, C$_{arom}$), 128.8 (d, C$_{arom}$), 128.7 (d, C$_{arom}$), 128.65 (d, C$_{arom}$), 128.62 (d, C$_{arom}$), 128.5 (d, C$_{arom}$), 128.4 (d, C$_{arom}$), 128.2 (d, C$_{arom}$), 127.9 (d, C$_{arom}$), 127.8 (d, C$_{arom}$), 127.7 (d, C$_{arom}$), 127.5 (d, C$_{arom}$), 127.3 (d, C$_{arom}$), 127.1 (d, C$_{arom}$), 126.9 (d, C$_{arom}$), 126.8 (d, C$_{arom}$), 127.6 (d, C$_{arom}$), 126.4 (d, C$_{arom}$), 59.6 (d, CH$_\alpha$-Phe$_2$, A), 59.5 (d, CH$_\alpha$-Phe$_2$, a), 53.6 (d, CH$_\alpha$-Phe$_1$, a), 53.4 (d, CH$_\alpha$-Phe$_1$, A), 52.45 (c, CO$_2$CH$_3$-Phe$_2$, A), 52.42 c, CO$_2$CH$_3$-Phe$_2$, a), 52.2 (c, CO$_2$CH$_3$-Phe$_1$, a), 52.0 (c, CO$_2$CH$_3$-Phe$_1$, A), 37.7 (t, CH$_2$-Phe$_1$, a), 37.4 (t, CH$_2$-Phe$_1$, A), 37.3 (t, CH$_2$-Phe$_2$, a), 36.5 (t, CH$_2$-Phe$_2$, A), ppm IR v 3436, 3027, 2950, 1744, 1639, 1535, 1436, 1368, 1219, 754, 701 cm$^{-1}$.

ME (ES$^+$), m/e=581 ([MH]$^+$, 100%), 603 ([MH]$^+$, 36%),

EA calculated for $C_{34}H_{32}N_2O_5S$: C, 70.32; H, 5.55; N, 4.82; S, 5.52. Found: C, 70.25; H, 5.49; N, 4.69; S, 5.81.

Example 4

Methyl (S,S)-3-(1H-Indol-3-yl)-2-{[2'-(2-(1H-Indol-3-yl)-1-methoxycarbonyl-ethylthiocarbamoyl)-biphenyl-2-carbothioyl]-amino}-propionate (3)

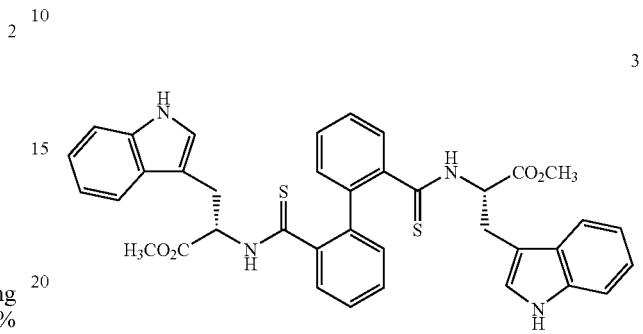

It was obtained, together with compound 4, following the general procedure, with a yield of 37% after column chromatography (hexane/AcOEt gradient: 9/1 up to hexane/AcOEt gradient: 3/7). Pale yellow solid.

m.p.=125-127° C.

$[\alpha]_D = -31$ (c=0.25, MeOH).

$^1$H-NMR (300 MHz, DMSO-d$_6$) δ: 10.82 (s, 2H, 2-NH-Indol), 10.71 (s wide, 2H, 2-NH-Trp), 7.46-7.20 (m, 10H, H$_{arom}$), 7.10-6.97 (m, 8H, H$_{arom}$), 5.07 (m, 2H, CH$_\alpha$-Trp), 3.50 (s, 6H, CO$_2$CH$_3$), 2.97 (m, 1H, C(H$_\alpha$H$_\beta$)-Trp), 2.73 (m, 1H, C(H$_\alpha$H$_\beta$)-Trp), ppm.

$^{13}$C-NMR (75 MHz, DMSO-d$_6$) δ: 199.3 (s, 2C, CS), 170.1 (s, 2C, CO), 141.1 (s, 2C, C$_{arom}$), 136.1 (s, 6C, C$_{arom}$), 128.9 (d, 2C, C$_{arom}$), 127.6 (d, 2C, C$_{arom}$), 126.8 (d, 2C, C$_{arom}$), 123.6 (s, 4C, C$_{arom}$), 121.1 (d, 4C, C$_{arom}$), 118.5 (s, 2C, C$_{arom}$), 117.9 (d, 2C, C$_{arom}$), 111.5 (d, 2C, C$_{arom}$), 59.1 (d, 2C, CH$_\alpha$-Trp), 51.0 (c, 2C, CO$_2$CH$_3$), 26.5 (t, 2C, CH$_2$-Trp), ppm IR v 3413, 3012, 2949, 2846, 1737, 1621, 1513, 1457, 1434, 1373, 1216, 1095, 1009, 957, 743 cm$^{-1}$.

ME (ES$^+$), m/e=675 ([MH]$^+$, 100%), 697 ([MNa]$^+$, 9%).

EA calculated for $C_{38}H_{34}N_4O_4S_2$: C, 67.63; H, 5.08; N, 8.30; S, 9.50. Found: C, 67.51; H, 5.32; N, 8.04; S, 9.21.

Example 5

Methyl (S,S)-3-(1H-Indol-3-yl)-2-{[2'-(2-(1H-Indol-3-yl)-1-methoxycarbonyl-ethylthiocarbamoyl)-biphenyl-2-carbonyl]-amino}-propionate (4)

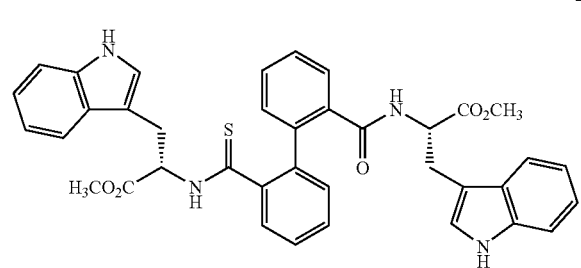

It was obtained together with compound 3, following the general procedure, with a yield of 35% after column chromatography (hexane/AcOEt gradient: 9/1 up to hexane/AcOEt gradient: 3/7). Pale yellow solid.

$[\alpha]^{25}_D = -12$ (c=0.15, MeOH).

$^1$H-NMR (300 MHz, CD$_3$OD) δ: 10.80 (s, 1H, NH-Indol), 10.72 (s, 1H, NH-Indol), 10.70 (s wide, 1H, NH-Trp$_2$), 8.80 (d, 1H, $J_{NH,CH\alpha}$=6.8, NH-Trp$_1$), 7.67 (m, 2H, H$_{arom}$), 7.59-7.29 (m, 8H, H$_{arom}$), 7.28-7.03 (m, 8H, H$_{arom}$), 5.32 (m, 1H, CH$_\alpha$-Trp$_2$), 4.86 (m, 1H, CH$_\alpha$-Trp$_1$), 3.77 (s, 3H, CO$_2$CH$_3$), 3.72 (s, 3H, CO$_2$CH$_3$), 3.37 (m, 1H, CH$_\alpha$H$_\beta$-Trp$_2$; 1H, CH$_\alpha$H$_\beta$-Trp$_1$), 3.12 (m, 1H, CH$_\alpha$H$_{\beta\text{-}Trp1}$), 3.02 (m, 1H, CH$_\alpha$H$_\beta$-Trp$_2$), ppm.

$^{13}$C-NMR (75 MHz, CD$_3$OD) δ: 202.0 (s, CS), 173.6 (s, CO), 172.4 (s, CO), 172.3 (s, CO), 143.4 (s, 2C, C$_{arom}$), 138.0 (s, 4C, C$_{arom}$), 136.4 (s, C$_{arom}$), 130.8 (d, C$_{arom}$), 130.7 (d, C$_{arom}$), 130.5 (d, C$_{arom}$), 129.8 (d, C$_{arom}$), 129.0 (d, C$_{arom}$), 128.5 (d, C$_{arom}$), 128.6 (d, C$_{arom}$), 124.4 (d, C$_{arom}$), 122.4 (d, 2C, C$_{arom}$), 119.8 (d, C$_{arom}$), 119.3 (d, C$_{arom}$), 119.2 (d, C$_{arom}$), 112.4 (d, 2C, C$_{arom}$), 110.7 (s, C$_{arom}$), 110.4 (s, C$_{arom}$), 60.7 (d, CH$_\alpha$-Trp$_2$), 55.2 (d, CH$_\alpha$-Trp$_1$), 52.7 (c, 2C, CO$_2$CH$_3$), 28.3 (t, 2C, CH$_2$-Trp$_1$), 27.9 (t, CH$_2$-Trp$_2$), ppm IR ν 3413, 3054, 2949, 1737, 1640, 1522, 1491, 1457, 1436, 1354, 1217, 1094, 1009, 744 cm$^{-1}$.

ME (ES$^+$), m/e=659 ([MH]$^+$, 100%), 681 ([MNa]$^+$, 16%).

EA calculated for C$_{38}$H$_{34}$N$_4$O$_5$S: C, 69.28; H, 5.20; N, 8.50; S, 4.87. Found: C, 69.13; H, 5.41; N, 8.58; S, 5.01.

Example 6

Methyl (S,S)-2-{[2'-(1-methoxycarbonyl-2-methyl-propylthiocarbamoyl)-biphenyl-2-carbothioyl]-amino}-3-methyl-butyrate (5)

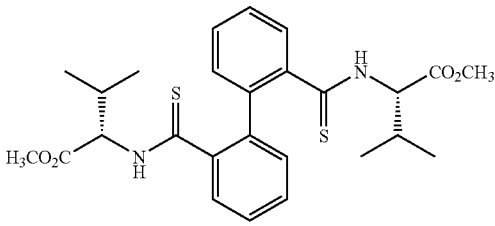

5

It was obtained together with compound 6, with a yield of 67% after column chromatography (hexane/AcOEt gradient: 9/1 up to hexane/AcOEt gradient: 4/6), using the general method described. Pale yellow solid.

$[\alpha]^{25}_D = +3$ (c=0.28, MeOH).

$^1$H-NMR (300 MHz, DMSO-d$_6$) δ: 10.45 (s wide, 2H, 2-NH-Val), 7.36 (m, 6H, H$_{arom}$), 7.11 (m, 2H, H$_{arom}$), 4.72 (m, 2H, CH$_\alpha$-Val), 3.60 (s, 6H, CO$_2$CH$_3$), 2.03 (m, 1H, CH-Val), 0.81 (s wide, 6H, CH(CH$_3$)(CH$_3$)-Val), 0.72 (s wide, 6H, CH(CH$_3$)(CH$_3$)-Val), ppm $^{13}$C-NMR (75 MHz, DMSO-d$_6$) δ: 200.3 (s, 2C, CS), 169.7 (s, 2C, CO), 141.3 (s, 2C, C$_{arom}$), 136.5 (s, 2C, C$_{arom}$), 129.3 (d, 2C, C$_{arom}$), 128.8 (d, 2C, C$_{arom}$), 128.0 (d, 2C, C$_{arom}$), 127.4 (d, 2C, C$_{arom}$), 64.2 (d, 2C, CH$_\alpha$-Val), 51.7 (c, 2C, CO$_2$CH$_3$), 29.8 (d, 2C, CH(CH$_3$)$_2$-Val), 18.8 (c, CH(CH$_3$)(CH$_3$)-Val), 18.5 (c, CH(CH$_3$)(CH$_3$)-Val), ppm.

IR ν 3437, 3005, 2965, 2873, 1742, 1633, 1525, 1467, 1434, 1376, 1260, 1207, 1152, 1111, 1004, 748 cm$^{-1}$.

ME (ES$^+$), m/e=501 ([MH]$^+$, 100%), 523 ([MH]$^+$, 35%).

EA calculated for C$_{26}$H$_{32}$N$_2$O$_4$S$_2$: C, 62.37; H, 6.44; N, 5.60; S, 12.81. Found: C, 62.18; H, 6.61; N, 5.58; S, 12.68.

Example 7

Methyl (S,S)-2-{[2'-(1-methoxycarbonyl-2-methyl-propylthiocarbamoyl)-biphenyl-2-carbonyl]-amino}-3-methyl-butyrate (6)

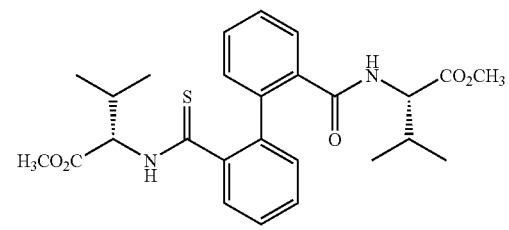

6

It was obtained together with compound 5, following the general procedure, with a yield of 11% after column chromatography (hexane/AcOEt gradient: 9/1 up to hexane/AcOEt gradient: 4/6). Pale yellow solid.

$^1$H-NMR (300 MHz, CD$_3$OD) δ: 10.57 (s wide, 1H, NH-Val$_2$), 8.67 (d, 1H, $J_{NH,CH}$=8.3, NH-Val$_1$), 7.54 (m, 1H, H$_{arom}$), 7.41 (m, 5H, H$_{arom}$), 7.27-7.09 (m, 2H, H$_{arom}$), 4.85 (m, 1H, CH$_\alpha$-Val$_2$), 4.27 (m, 1H, CH$_\alpha$-Val$_1$), 3.69 (s, 3H, CO$_2$CH$_3$), 3.67 (s, 3H, CO$_2$CH$_3$), 2.06 (m, 2H, CH-Val), 0.87 (m, 6H, CH(CH$_3$)$_2$-Val), 0.75 (m, 6H, CH(CH$_3$)$_2$-Val), ppm $^{13}$C-NMR (75 MHz, CD$_3$OD) δ: 203.0 (s, CS), 173.2 (s, CO), 172.8 (s, CO), 172.0.8 (s, CO), 143.8 (s, C$_{arom}$), 140.4 (s, C$_{arom}$), 138.7 (s, C$_{arom}$), 136.8 (s, C$_{arom}$), 131.2 (d, C$_{arom}$), 130.9 (d, 2C, C$_{arom}$), 130.0 (d, C$_{arom}$), 128.9 (d, 2C, C$_{arom}$), 128.8 (d, 2C, C$_{arom}$), 65.4 (d, CH$_\alpha$-Val$_2$), 59.8 (d, CH$_\alpha$-Val$_1$), 52.4 (c, 2C, CO$_2$CH$_3$), 32.1 (d, CH(CH$_3$)$_2$-Val), 31.8 (d, CH(CH$_3$)$_2$-Val), 19.4 (c, CH(CH$_3$)(CH$_3$)-Val), 19.2 (c, CH(CH$_3$)(CH$_3$)-Val), 19.1 (c, CH(CH$_3$)(CH$_3$)-Val), 18.6 (c, CH(CH$_3$)(CH$_3$)-Val), ppm.

IR ν 3430, 3021, 2963, 2923, 2873, 1742, 1642, 1532, 1468, 1435, 1376, 1315, 1262, 1207, 1155, 1100, 1020, 801, 756 cm$^{-1}$.

ME (ES$^+$) m/e=485 ([MH]$^+$, 100%).

EA calculated for C$_{26}$H$_{32}$N$_2$O$_5$S: C, 64.44; H, 6.66; N, 5.78; S, 6.62. Found: C, 64.68; H, 6.76; N, 5.53; S, 6.65.

Example 8

Methyl (S,S)-3-(4-hydroxy-phenyl)-2-{2'-[2-(4-hydroxy-phenyl)-1-methoxycarbonyl-ethylthiocarbamoyl]-biphenyl-2-carbothioyl]-amino}-propionate (7)

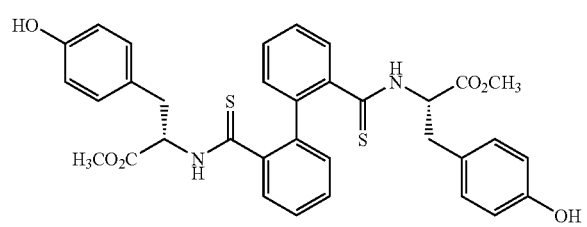

7

It was obtained together with compound 8, following the general procedure, with a yield of 3% after column chromatography (CH$_2$Cl$_2$/AcOEt gradient: 9/1 up to CH$_2$Cl$_2$/AcOEt gradient: 1/1). Pale yellow solid.

m.p.=62-65° C. [α]$^{25}_D$=−4 (c=0.15, MeOH).

$^1$H-NMR (300 MHz, CDCl$_3$, 30° C., mixture of conformers A+a, 3:2) δ: 8.97 (d, 0.8H, J$_{NH,CH\alpha}$=8.0, NH, a), 7.80 (d, 1.2H, J$_{NH,CH\alpha}$=7.0, NH, A), 7.46-7.02 (m, 8H, H$_{arom}$, A+a), 6.97 (d, 1.6H, J$_{ortho}$=8.3, H$_{arom}$-Tyr, a), 6.88 (d, 2.4H, J$_{ortho}$=8.3, H$_{arom}$-Tyr, A), 6.71 (d, 2.4H, J$_{ortho}$=8.3, H$_{arom}$-Tyr, A), 6.70 (d, 1.2H, J$_{ortho}$=8.3, H$_{arom}$-Tyr, A), 5.32 (m, 1.2H, C$\underline{H}_\alpha$-Tyr, A), 5.22 (m, 0.8H, C$\underline{H}_\alpha$-Tyr, a), 3.67 (s, 3.6H, CO$_2$C$\underline{H}_3$, A), 3.56 (s, 2.4H, CO$_2$C$\underline{H}_3$, a), 3.15 (A of ABX, 0.8H, J$_{H\alpha,H\beta}$=14.1, J$_{H\alpha,CH\alpha}$=8.1, C($\underline{H}_\alpha$H$_\beta$)-Tyr, a), 3.14 (B of ABX, 0.8H, J$_{H\beta,H\alpha}$=14.1, J$_{H\beta,CH\alpha}$=5.2, C(H$_\alpha$$\underline{H}_\beta$)-Tyr, a), 2.92 (A of ABX, 1.2H, J$_{H\alpha,H\beta}$=14.1, J$_{H\alpha,CH\alpha}$=8.1, C($\underline{H}_\alpha$H$_\beta$)-Tyr, A), 2.74 (B of ABX, 1.2H, J$_{H\beta,H\alpha}$=14.1, J$_{H\beta,CH\alpha}$=5.2, C(H$_\alpha$$\underline{H}_\beta$)-Tyr, A), ppm.

$^{13}$C-NMR (75 MHz, CDCl$_3$, 30° C. mixture of conformers A+a, 3:2) δ: 200.2 (s, CS, a), 200.0 (s, CS, A), 170.9 (s, CO, A), 170.7 (s, CO, a), 154.7 (s, C$_{arom}$, A), 153.7 (s, C$_{arom}$, a), 141.6 (s, C$_{arom}$, A), 141.5 (s, C$_{arom}$, a), 137.2 (s, C$_{arom}$, A), 137.0 (s, C$_{arom}$, a), 130.4 (d, C$_{arom}$, A), 130.2 (d, C$_{arom}$, a), 129.9 (d, C$_{arom}$, a), 129.8 (d, C$_{arom}$, A), 129.2 (d, C$_{arom}$, A), 129.1 (d, C$_{arom}$, a), 127.8 (d, C$_{arom}$, a), 127.7 (d, C$_{arom}$), 127.7 (d, C$_{arom}$, A), 127.6 (d, C$_{arom}$, A), 127.5 (d, C$_{arom}$, a), 115.5 (d, C$_{arom}$, A), 115.4 (d, C$_{arom}$, a), 59.3 (d, C$\underline{H}_\alpha$-Tyr, a), 59.1 (d, C$\underline{H}_\alpha$-Tyr, A), 52.5 (c, CO$_2$C$\underline{H}_3$, a), 52.4 (c, CO$_2$C$\underline{H}_3$, A), 36.0 (t, C$\underline{H}_2$-Tyr, A), 35.7 (t, C$\underline{H}_2$-Phe, a), ppm IR ν 3426, 3025, 2951, 1743, 1631, 1530, 1496, 1434, 1374, 1215, 956, 749, 700 cm$^{-1}$.

ME (ES$^+$), m/e=629 ([MH]$^+$, 100%), 651 ([MNa]$^+$, 15%).

EA calculated for C$_{34}$H$_{32}$N$_2$O$_6$S$_2$: C, 64.95; H, 5.13; N, 4.46; S, 10.20. Found: C, 65.21; H, 5.28; N, 4.51; S, 10.51.

Example 9

Methyl (S,S)-3-(4-hydroxy-phenyl)-2-{2'-[2-(4-hydroxy-phenyl)-1-methoxycarbonyl-ethylthiocarbamoyl]-biphenyl-2-carbonyl]-amino}-propionate (8)

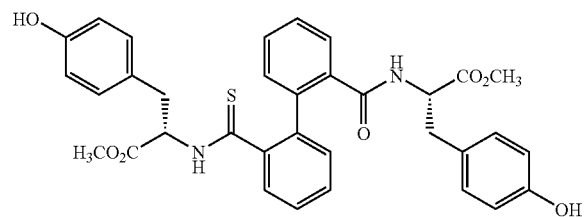

8

It was obtained together with compound 7, following the general procedure, with a yield of 9% after column chromatography (CH$_2$Cl$_2$/AcOEt gradient: 9/1 up to CH$_2$Cl$_2$/AcOEt gradient: 1/1). Pale yellow solid.

m.p.=87-91° C. [α]$^{25}_D$=−12 (c=0.51, MeOH).

$^1$H-NMR (300 MHz, CD$_3$OD) δ: 10.72 (s wide, 1H, NH-Tyr$_2$), 8.78 (d wide, 1H, NH-Tyr$_1$), 7.32 (m, 8H, H$_{arom}$), 7.02-6.76 (m, 4H, H$_{arom}$-Tyr), 6.68 (d, 4H, J$_{ortho}$=8.0, H$_{arom}$-Tyr), 5.06 (m, 1H, C$\underline{H}_\alpha$-Tyr$_2$), 4.55 (m, 1H, C$\underline{H}_\alpha$-Tyr$_1$), 3.57 (s, 3H, CO$_2$C$\underline{H}_3$-Tyr$_2$), 3.55 (s, 3H, CO$_2$C$\underline{H}_3$-Tyr$_1$), 3.02-2.59 (m, 2H, C($\underline{H}_\alpha$H$_\beta$)-Tyr$_2$; 1H C($\underline{H}_\alpha$H$_\beta$)-Tyr$_1$), 2.37 (m, 1H, C(H$_\alpha$$\underline{H}_\beta$)-Tyr$_1$), ppm.

$^{13}$C-NMR (75 MHz, CD$_3$OD) δ: 202.2 (s, CS), 171.3 (s, CO), 170.2 (s, CO), 170.1 (s, CO), 155.5 (s, C$_{arom}$), 155.4 (s, C$_{arom}$), 141.7 (s, C$_{arom}$), 141.5 (s, C$_{arom}$), 138.4 (s, 3C, C$_{arom}$), 136.4 (s, C$_{arom}$), 134.4 (d, C$_{arom}$), 129.3 (d, 2C, C$_{arom}$), 129.0 (d, 2C, C$_{arom}$), 128.7 (d, C$_{arom}$), 128.0 (d, C$_{arom}$), 127.0 (d, C$_{arom}$), 126.7 (d, 2C, C$_{arom}$), 114.4 (d, 2C, C$_{arom}$), 59.7 (d, C$\underline{H}_\alpha$-Tyr$_2$), 53.9 (d, C$\underline{H}_\alpha$-Tyr$_1$), 50.8 (c, CO$_2$C$\underline{H}_3$), 50.7 (c, CO$_2$C$\underline{H}_3$), 35.6 (t, C$\underline{H}_2$-Tyr$_2$), 35.1 (t, C$\underline{H}_2$-Tyr$_1$), ppm IR ν 3427, 3014, 2949, 1735, 1635, 1515, 1437, 1363, 1223, 755, 701 cm$^{-1}$.

ME (ES$^+$), m/e=613 ([MH]$^+$, 100%), 635 ([MNa]$^+$, 25%).

EA calculated for C$_{34}$H$_{32}$N$_2$O$_7$S: C, 66.65; H, 5.26; N, 4.57; S, 5.23. Found: C, 66.86; H, 5.39; N, 4.61; S, 5.51.

Example 10

Enzyme Activity Test: Inhibition of Calpain

The calpain inhibition capacity has been quantified in terms of the value of IC$_{50}$, which is defined as the concentration of inhibitor that reduces the catalytic activity of an enzyme by half. The lower the value of IC$_{50}$, the more powerful the inhibitor. Inhibition results on calpain I (the most relevant from a physiological point of view) of some compounds of the present invention are shown in table 1 and in FIG. 1.

TABLE 1

Inhibition results on calpain of compounds forming the object of this invention

| Compounds | IC$_{50}$ |
|---|---|
| 1 | 94 μM |
| 2 | 63 μM |
| 3 | 38 pM (=0.038 nM) |
| 4 | 69 nM |
| 5 | 71 nM |
| 6 | 52 pM (=0.052 nM) |
| 7 | 796 nM |
| 8 | 12 μM |

In order to carry out the inhibition test on calpains, we used the EnzCheck® Protease Assay Kit E-338 from Molecular Probes. This kit contains casein marked with BODIPY FL®, freeze-dried from phosphate buffer. Also used as a digestion buffer was Tris-HCl at pH 7.8, containing 2 mM of sodium azide. The calpain I from porcine erythrocytes or calpain II from porcine kidney that were used are commercial products from CALBIOCHEM®. The enzyme stock solution contained 20 mM of imidazol-HCl buffer, pH 6.8, 1 mM EDTA, 1 mM EGTA, 5 mM β-mercaptoethanol, 30% in glycerol.

The synthetic inhibitors were dissolved in 250 μL of DMSO. The tests were conducted on 96-well microplates in a final volume of 200 μL. In order to carry out the test, aliquots of stock solution of calpain were added to 150 μL of a 10 μg/μL solution in digestion buffer in order to obtain a final concentration of 50 ng/mL of enzyme. Minimum quantities were added, between 5 and 20 μL of inhibitor solution in DMSO, previously diluted in order to achieve the desired final concentration of inhibitor, and digestion buffer was added until a volume of 190 μL was achieved. The test commenced by adding 10 μL of 0.05 M CaCl$_2$ solution. For each inhibitor, separate measurements excluding inhibitor, calpain and calcium solution were taken as blanks. All measurements were made in triplicate.

The fluorescence measurements were made in a SPECTRAFLUOR TECAN Corp 93382 spectrum fluorimeter, exciting at 485 nm and taking the reading at 530 nm. The measurement was made over 20 cycles until the measurement of all wells was completed. Stirring was orbital type and took place each cycle.

ABBREVIATIONS

Stated below are the meaning of the abbreviations used:
EA: Element analysis
CANP: Calcium activated neutral protease
DMSO: Dimethylsulphoxide
EDTA: Ethylenediaminetetraacetic acid
EGTA: Ethylene-bis-(oxyethylenenitrile)tetraacetic acid
ME: Mass spectrum
ES: Electro-spray
IR: Infrared
NMDA: N-methyl-D-aspartate
m.p.: melting point
Tris: Tris(hydroxymethyl)aminomethane
$^1$H-NMR: Proton nuclear magnetic resonance
$^{13}$C-NMR: Carbon-13 nuclear magnetic resonance

The invention claimed is:

1. A compound of formula I, which has a 2,2'-disubstituted biphenyl structure,

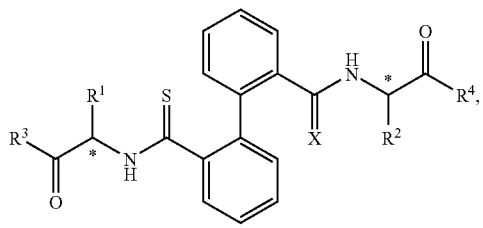

wherein:
the group X is oxygen (O) or sulphur (S), indifferently,
the groups $R^1$ and $R^2$ are the same or different and are independently selected from among the groups H, alkyl of between 1 and 10 carbon atoms, aryl, and arylalkyl, when applicable (that is, when $R^1$ or $R^2 \neq H$), the asterisk (*) represents a stereogenic center, of configuration (R) or (S), indifferently,
the groups $R^3$ and $R^4$ are the same or different and are independently selected from among the groups
H,
alkyl of between 1 and 6 carbon atoms,
aryl,
arylalkyl,
$NH_2$,
$NHR^5$ in which $R^5$ represents an alkyl or aryl group,
$NR^6R^7$ in which $R^6$ and $R^7$ represent two alkyl or aryl groups, identical or different, or forming a cyclic system,
OH,
$OR^8$ in which $R^8$ represents an alkyl or aryl group;
and any of the conformational isomers (atropisomers) of said compound of formula I.

2. A compound according to claim 1 having formula I and is selected from among
Methyl (S,S)-3-phenyl-2-{[2'-(2-phenyl-1-methoxycarbonyl-ethylthio-carbamoyl)-biphenyl-2-carbothioyl]-amino}-propionate (1),
Methyl (S,S)-3-phenyl-2-{[2'-(2-phenyl-1-methoxycarbonyl-ethylthio-carbamoyl)-biphenyl-2-carbonyl]-amino}-propionate (2),
Methyl (S,S)-3-(1H-Indol-3-yl)-2-{[2'-(2-(1H-Indol-3-yl)-1-methoxycarbonyl-ethylcarbamoyl)-biphenyl-2-carbothioyl]-amino}-propionate (3),
Methyl (S,S)-3-(1H-Indol-3-yl)-2-{[2'-(2-(1H-Indol-3-yl)-1-methoxycarbonyl-ethylcarbamoyl)-biphenyl-2-carbonyl]-amino}-propionate (4),
Methyl (S,S)-2-{[2'-(1-methoxycarbonyl-2-methyl-propylthiocarbamoyl)-biphenyl-2-carbothioyl]-amino}-3-methyl-butyrate (5),
Methyl (S,S)-2-{[2'-(1-methoxycarbonyl-2-methyl-propylthiocarbamoyl)-biphenyl-2-carbonyl]-amino}-3-methyl-butyrate (6),
Methyl (S,S)-3-(4-hydroxy-phenyl)-2-{2'-[2-(4-hydroxy-phenyl)-1-methoxycarbonyl-ethylthiocarbamoyl]-biphenyl-2-carbothioyl]-amino}-propionate (7),
and
Methyl (S,S)-3-(4-hydroxy-phenyl)-2-{2'-[2-(4-hydroxy-phenyl)-1-methoxycarbonyl-ethylthiocarbamoyl]-biphenyl-2-carbonyl]-amino}-propionate (8).

3. Method for the therapeutic treatment of a degenerative disease by inhibiting calpain which comprises administering to a subject an effective amount of an inhibitor compound of formula I as defined in claim 1.

4. Method according to claim 3, wherein the degenerative disease is cerebral ischaemia, cardiac ischaemia, Alzheimer, Parkinson, muscular distrophy, cataracts and multiple sclerosis.

* * * * *